United States Patent [19]

Van Beeck et al.

[11] 4,274,747
[45] Jun. 23, 1981

[54] METHOD AND DEVICE FOR INSPECTING A MOVING SHEET MATERIAL FOR STREAKLIKE DEFECTS

[75] Inventors: Walter P. Van Beeck, Sinaai; Alfons J. Dictus, Ekeren; Maurits Geens, Haacht; Roger J. Simons, Antwerp; Jean Burtin, Mol, all of Belgium

[73] Assignee: AGFA-GEVAERT N.V., Mortsel, Belgium

[21] Appl. No.: 50,792

[22] Filed: Jun. 21, 1979

[30] Foreign Application Priority Data

Jun. 26, 1978 [GB] United Kingdom ............... 27863/78

[51] Int. Cl.³ .......................................... G01N 21/89
[52] U.S. Cl. .................................... 356/431; 250/563; 356/434
[58] Field of Search ............... 356/429, 430, 431, 239, 356/444, 434; 250/563, 572

[56] References Cited

U.S. PATENT DOCUMENTS

| 3,199,401 | 8/1965 | Sleighter et al. | 250/572 X |
| 3,754,146 | 8/1973 | Chow | 356/239 X |
| 4,173,441 | 11/1979 | Wolf | 356/431 |

FOREIGN PATENT DOCUMENTS

2363422  6/1975  Fed. Rep. of Germany ...... 356/431 X

Primary Examiner—John K. Corbin
Assistant Examiner—Bruce Y. Arnold
Attorney, Agent, or Firm—William J. Daniel

[57] ABSTRACT

Subtle streaklike defects are detected in running webs and sheets by transversely scanning distinct lateral sections of the webs or sheets by means of lines of radiant energy extending parallel with the direction of movement of the webs or sheets. Transmitted or reflected radiation is received on corresponding photocells that move synchronously with the lines of radiant energy. During each scan of each section of the webs or sheets, a large number of comparisons occur between the output signals of each photocell at a given first lateral position and at a second lateral position that is separated from the first one by a distance that is of the order of magnitude of the width and preferably half the width, of a streaklike defect to be identified.

15 Claims, 12 Drawing Figures

METHOD AND DEVICE FOR INSPECTING A MOVING SHEET MATERIAL FOR STREAKLIKE DEFECTS

This invention relates to a method and a device for inspecting a moving sheet material for streaklike defects, comprising means for directing radiant energy on one surface of the sheet material and photocell means for measuring at distinct lateral positions of the sheet material the intensity of the radiation after transmission of the radiation through, or after reflection from the surface of the sheet material.

Known devices operate satisfactorily for the detection of rather coarse speck- and streaklike defects in moving sheets since in such cases the signal-to-noise ratio of the output signals of the photocells is sufficiently great to enable the signals, after their amplification, to be compared with a predetermined reference signal in order to identify a defect. These defect identifying signals may either be stored in digital or analog form in a memory together with the exact address of the defect, or they may directly be signalled during, e.g. the coating of webs in order to halt or to re-adjust the coater, or they may directly control a sorting mechanism as in the inspection of sheets cut from a coated web. As examples of rather coarse defects can be mentioned specklike defects caused by the inclusion of a foreign body, e.g. a dust particle in a coated layer, or a dry spot, e.g. an air bubble included during the coating of a layer on a support.

In those cases, however, where very minute defects have to be identified, fluttering of the material at the place of measurement and noise of the electronic circuitry may cause variations in the output signals of the photocells that are of the same order of magnitude as those caused by a sheet defect.

It is known to use electronic correlation techniques for improving the signal-to-noise ratio of the defect identifying signals. A basic condition for the operation of such techniques is that the defect to be identified should be recursive during a number of, say at least 5, successive scans. This means that the defects have to be of protracted extent in the machine direction, that is in the coating direction in the case of the inspection of coated layers. In other words, only streaklike defects can be more readily distinguished from noise and flutter signals by electronic correlation of each photocell signal.

It is further known that the identification of very subtle streaklike defects still raises difficulties because fluttering of a moving sheet material over a distance of, say 0.1 mm, is capable of producing output signals that are not discernable from true defect signals, in spite of electronic correlation.

As an example of very subtle streaklike defects, there can be mentioned streaklike irregularities, that occur at the coating on a web of a layer, or of a combination of layers as the case may be, by means of a socalled cascade or slide hopper coater. In certain application fields, notably in photography, very stringent requirements are put to the uniformity of a coated layer, and it is shown that photocell signals resulting from streaklike thickness deviations of an order of magnitude of 0.1%, even when correlated, are not discernable from signals that are caused by the noise of the electronic circuitry and caused above all by the fluttering of the web at the place of measurement.

As to the occurrence of the mentioned defect in the said coating technique, it is assumed that the most important cause of such a defect is the passage of a web splice through the coating bead. It appears that a web splice entrains air in the coating bead and that such air may remain there for quite long periods, in some circumstances covering hundreds of meters of material, so that the coating at that area is disturbed in a very characteristic way, namely a zone of thinner coating is produced on the web and immediately adjacent to said thinner zone there is a zone of thicker coating. The cross-section of said disturbance is in a number of cases almost sinusoidal. Another typical cross-section of such disturbance is a more pronounced thinner zone situated between two less pronounced thicker zones.

Considering that, in the manufacturing of delicate materials, such as radiographic film or film for graphic reproduction techniques, thickness variations in a coated layer of the order of magnitude of 0.1% as mentioned above should be identified, it will be understood that the signal-to-noise characteristics of common detection systems do not enable a reliable retrieval of the mentioned defect. A typical photoelectric detection system for purposes of this discussion can comprise means for directing onto one side of the sheet material a spot of radiation that sweeps periodically across the surface of the moving sheet material in order to transversely scan the material or, alternatively, a large plurality of distinct point light sources that are mounted stationarily in line across the path of the sheet material and are energized in sequence in order to transversely scan the material from one lateral edge to the other.

As to the fluttering of a moving sheet material, two aspects have to be taken into account. First, the vibration of the material in a direction normal to the tangent plane to two successive rollers over which the material is conveyed and between which the photocells are arranged. The peak-to-peak amplitude of vibration may reach values up to 5 mm in extreme cases. Second, fluttering is not constantly present at the place of measurement and may even completely disappear for periods exceeding several hours. However, a web splicing operation, a sudden operation of a device for steering the lateral web position, etc., may induce web flutter whereby false read-out signals of the photocells are obtained. As a consequence of the frequency range of web flutter, namely from D.C. to about 20 Hz, usual correlation techniques have failed so far to improve the discernability of streaklike defects of an order of magnitude as mentioned hereinbefore.

A further difficulty that complicates the identification of very minute defects is the so-called "profile" of a material to be inspected. This term means in practice that the thickness of a given sheet material or of a layer coated thereon may slightly but progressively increase or decrease from one edge to the other. In case this variation is small, say 1 to 3%, it should not be considered as a defect in many cases since, for instance, in the coating of a photographic film, the film is longitudinally slit at a later stage into a number of narrower strips wherein the absolute thickness variation of a coated layer in the transverse direction is negligible. Since, however, known defect inspection systems are based on the steps of measuring of the thickness at a plurality of transversely spaced positions on a web, comparing each measurement signal with a reference signal, and then "normalizing" the resulting comparison signals in order to eliminate the influence of the mentioned coating profile, it will be understood that the electronic circuitry of the measuring system is greatly complicated as a consequence of the normalization at each measuring position, which requires substantial memory functions. Alternatively, the reference signals themselves may be normalized as a function of the coating profile.

Said "normalization" has also to occur in case the inspection system itself has a non-linear response over the scanning width, for instance as a consequence of the use of a plurality of photoelectric cells that are closely spaced in a row that extends transversely of the sheet material and/or as a consequence of the use of a plurality of distinct light sources that are energized in sequence for scanning the material. The sensitivity of the different channels that each comprise a lamp, a photocell and a corresponding amplifier may slightly differ from one channel to the other, and thus a "normalization" of the signal processing of the system is required.

The present invention aims to provide a method and a device that are based on a new optical and electronic approach of the measuring system in order to obtain a simple system that shows a great sensitivity for the detection in moving sheet materials of subtle defects of protracted extent and that, depending on the case, may be used in conjunction with known electronic correlation systems in order to further increase the sensitivity of the system, that is to improve the signal-to-noise ratio. It is a further aim of the invention to provide a method and a device that are adjustable as a function of the width of a characteristic streaklike defect, thereby to increase the sensitivity of the system by a factor up to 6 dB.

In accordance with the present invention, there is provided a method of inspecting sheet material for streaklike defects during travel of such material along a certain path, which method comprises scanning the material across at least part of the width of its path by means of one or more beams of radiation each of which at any given instant irradiates a narrow elongated zone (elongated in the direction of travel of the material) within the width of the said path, receiving quanta of such radiant energy, modulated by adjacent successively irradiated zones of the material, on a photocell to derive from such photocell a multiplicity of sequential signals each representative of a particular one of said zones, and comparing successive said signals with each other and using amplitude differences between compared signals to provide an indication of the presence of said defects.

The invention includes a method which comprises:

projecting on the moving sheet material a narrow elongated beam of radiant energy having its length direction extending parallel to the direction of movement of the sheet material, receiving the radiant energy of said beam on a photocell after said radiant energy has been modulated by the sheet material, periodically altering the position at which the material is irradiated thereby to transversely scan the said sheet material over at least a portion of its width, dividing the output signal of the photocell during scanning into a multiplicity of discrete sequential signals each of which is representative of a particular longitudinal zone of the sheet material, and comparing the signals in successive pairs of such sequential signals with each other, and using the amplitude difference between such signal pairs to provide an indication of the severity of a streaklike defect.

The notion "streaklike defect in a moving sheet material" stands in the present specification for a line-wise defect that runs parallel with the direction of movement of the sheet material during its inspection. The term "sheet material" stands for webs that may have a length up to many hundreds of meters, as well as for a plurality of distinct sheets that may have been cut from such web and that may be inspected in succession.

The term "modulated" indicates that radiation is attenuated on its path towards the photocell, either by transmission through the sheet material or by reflection from the surface of said sheet material. Any defects present modify the attenuation.

The new optical approach as mentioned hereinbefore resides in the use of an elongated beam of radiation that runs parallel with the direction of movement of the sheet material. In this way, an optical integration of the information derived from streaklike defects is obtained whereby a considerable amplification of a signal pointing to a streaklike defect is obtained.

The new electronic approach as mentioned hereinbefore resides in making each time a comparison between successive output signals of the photocell during the scanning of the material. In this way a "relative" measurement is carried out, as distinct from the "absolute" measurements known in the art where each output signal of a photocell is compared with a reference signal, "normalised" as the case may be. Consequently, a web that is free of streaklike defects, but that may have a "coating profile" defect as defined hereinbefore, or have speck-like defects, is signalled as "acceptable" in the method according to the invention. A further advantage of the new electronic approach is that each measurement—that is a comparison of two successive signals—is a complete measurement that is independent of other information that may be only available after one complete scanning of the material, as in the case of signal normalization, so that the inspection frequency in the new method is high. In fact such frequency is determined by the quotient of the scanning time by the number of discrete comparisons. Suitable values for this inspection frequency are within a range of 100 to 10,000 Hz as will become further apparent from the description of the invention, so that it will be understood that the influence of web flutter, which is usually within a range of 0 to 20 Hz, can easily be filtered out by means of a suitable high-pass filter.

The term "narrow elongated zone" will be referred to in the description as an irradiated line for the sake of simplicity. It can be irradiated by a beam which can be regarded as a line of radiant energy. However it should be taken into account that the line has, apart from its length, also a definite width.

It is very suitable for the ratio between the length and the width of a said line to be in the range of 20 to 100. Suitable values for the width of the irradiated line are e.g. within the range of 0.05 to 3 mm.

In practice the multiplicity of sequential signals will be at least 100. It is suitable for example for the number of such signals to be within a range of 100 to 1000. Preferably the number of signals is even greater than 1000.

According to a first interesting embodiment of the method according to the invention, the derivation from the photocell or equivalent photo-sensitive means of a multiplicity of signals and a comparison of one signal with an immediately preceding or succeeding one is carried out by projecting two narrow elongate beams of radiant energy on the moving sheet material to irradiate two parallel lines spaced apart by a distance b, alternatingly and repeatedly energizing one beam and extinguishing the other beam during the scanning of the moving sheet material with the pair of beams, receiving the modulated energy of either beam on a single photocell, and demodulating the output signal of the photocell in synchronism with the switching frequency of both beams of radiant energy.

The distance b denotes the distance measured between the longitudinal centres of the pair of beams, and points thus also to the distance between the longitudinal centres of the corresponding longitudinal zones on the sheet material under comparison.

According to a second interesting embodiment of the invention, the derivation and comparison of signals is carried out by delaying an output signal of the photocell by a constant time delay $\tau$, comparing the delayed output signal of the photocell with the instant output signal that is produced after such time delay $\tau$, and using the amplitude difference between the instant and delayed output signals being compared as the measure of the severity of a streaklike defect, the time delay $\tau$ corresponding with a lateral spacing b between two zones of the web under inspection according to the expression:

$$b = S/T \cdot \tau$$

wherein S is the width of scanning and T is the time of scanning.

The distance b is preferably smaller than the width a of streaklike defects likely to be encountered. Suitable values of b are comprised between 0.15 and 1 times the width a, and in the case of a streaklike defect having an almost sinusoidal cross-section as will be described further in the specification, b is advantageously comprised between 0.4 and 0.6 times the width a, and optimally equals 0.5 times a.

According to a preferred embodiment of the method according to the invention, the distance b is adjusted in operation of the method thereby to obtain maximum sensitivity for a given type of streaklike defect. The method according to the invention may also comprise the simultaneous scanning of two or more widthwise adjacent longitudinal sections of a sheet material, each such section being covered by a photocell and an elongate beam of radiant energy as disclosed in the previous statements. In this way webs of large widths may be scanned. Occasional slight differences in the absolute sensitivity of different photocell circuits where more than one are employed are without importance since, as mentioned already hereinbefore, the method according to the invention is based on the comparison of the attenuation of a beam of radiant energy at two adjacent elongated zones of a sheet material so that the absolute accuracy of the measurement of each attenuation is without importance.

In accordance with the invention a device for inspecting a moving sheet material for streaklike defects comprises:

frame means that is mounted for oscillation in a direction transverse to the direction of movement of the sheet material, sources of radiant energy mounted on said frame and arranged for producing on the surface of a sheet material that is moving through the device, parallel spaced elongated beams of radiant energy extending in a direction parallel with the direction of movement of the sheet material through the device, photocells mounted on the frame and arranged for receiving radiation from a corresponding beam of radiant energy after each such beam has been modulated by the moving sheet material, means for oscillating the frame means with an oscillation amplitude that is at least equal to the spacing between two adjacent beams of radiant energy on the sheet material, thereby to transversely scan the material, and comparator means for comparing during each scan a multiplicity of pairs of distinct output signals of each photocell, the segments of which pairs are separated by a given time interval, to detect a difference in amplitude between the signals of such pairs.

Interesting features of the device according to the invention are as follows:

The device includes means for controlling the time interval between the signals being compared, which comprises a delay line in the electronic circuit of each photocell, and a differential type amplifier for comparing each delayed signal of a photocell with the instant output signal of the photocell occurring at the moment of comparison.

This control means comprises means for producing close to each beam of radiant energy a second, parallel, beam of radiant energy, thereby to impinge on the surface of a moving sheet material at least one pair of beams of radiant energy, with each photocell being so arranged that it is responsive to energy from a corresponding pair of beams, and the sources of radiant energy in each pair are alternatingly operative, thereby to alternatingly project first one and then the other beam of each pair of beams on the surface of the moving sheet material, and a demodulator for each photocell circuit, for demodulating the output signal of each photocell in synchronism with the switching of the operation of the beams of radiant energy.

The invention will be described hereinafter by way of example with reference to the accompanying drawings wherein.

Figure 1:
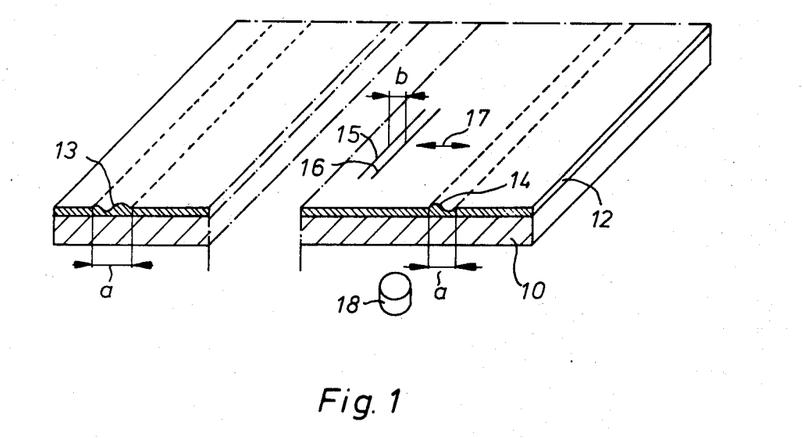
FIG. 1 is an enlarged partial cross-sectional view of a web with two different streaklike defects in a coating thereon.

Referring to FIG. 1, an enlarged partial cross-sectional view of a web 10 that runs in a direction indicated by the arrow 11, is shown. The web is provided with a coated layer 12 wherein two different kinds of streaklike defects have been illustrated by way of example. A first streaklike defect 13 is characterized by two slightly raised zones and one slightly recessed zone therebetween. A second streaklike defect 14 is characterized by an almost sinusoidal cross-section. In both cases the width of the defect is indicated by a. The length of such defects may range, in practice, from some meters to hundreds of meters, and as to the origin thereof we refer to the comments set forth in the introduction of the present application.

In accordance with the principle of the invention, the coated layer on the web is examined by means of an elongated beam of radiant energy, the lateral position of the projection of which on the coated layer is periodically moved thereby to scan the web, and reflected or transmitted energy is received on a photocell the output signal of which is divided into a multiplicity of discrete signals, and successive pairs of signals are compared with each other to detect a possible amplitude difference.

Referring to the example of FIG. 1, this examination occurs by means of two parallel linelike beams 15 and 16 of radiant energy that are produced on the outer surface of the layer 12 and that run also parallel with the direction 11 of movement of the web and that are oscillated in a direction indicated by the arrow 17 to scan a portion of the web width, thereby to examine the corresponding longitudinal section of the web.

The spectral wavelength of the light of beams 15 and 16 is thus selected that the radiant energy is liable to absorption in the layer 12 and not, or almost not, to absorption in the web 10.

Underneath the web 10 is mounted a photocell 18 that is responsive to radiation of the beams 15 and 16. The photocell is mounted for oscillation simultaneously with the lines 15 and 16, and has an angle of field in the transverse direction of the web that covers the distance between the two lines 15 and 16, and an angle of field in the longitudinal direction of the web that covers the length of the lines.

Figure 2:
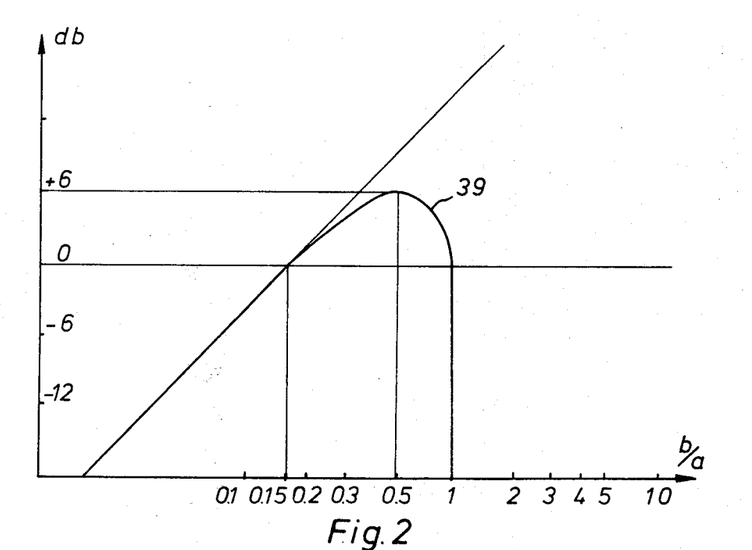
FIG. 2 is a diagram illustrating the sensitivity of a detection system for streaklike defects, as a function of the ratio between the lateral distance on the web between two parallel beams of radiant energy that transversely scan the web and the width of a streaklike defect.

The sensitivity of the described detection system for streaklike defects as a function of the ratio between the width a of a streaklike defect and the distance b between the centres of the two lines of radiant energy is illustrated by the curve 39 in FIG. 2 which is a diagram wherein the ordinate is a logarithmic scale representing the relative sensitivity in db, and the abcissa is a logarithmic scale representing the ratio b/a between the distance b between the two lines of radiant energy and the width a of a streaklike defect.

It may be seen that a ratio equal to 0.5 produces an output signal of the photocell that is 6 db, or by a factor of 2, greater than a ratio equal to 1 or greater, or than a ratio equal to 0.15 or smaller. In practice one will try to operate at a ratio between 0.4 and 0.6 whereas a ratio of 0.5 provides a maximum sensitivity (in the case of a streaklike defect with a sinusoidal cross-section). While it may at first sight appear difficult to adjust the detection arrangement in such a way that these conditions are fulfilled, considering the widely varying sizes of streaklike defects that may occur, practice shows that for a given coating composition, a given coating installation and in given coating conditions, nearly always the same size a of streaklike defects occurs, so that it is very well possible to adjust the distance b as a function of the type of streaklike defects that may be expected in each particular case.

Figure 3:
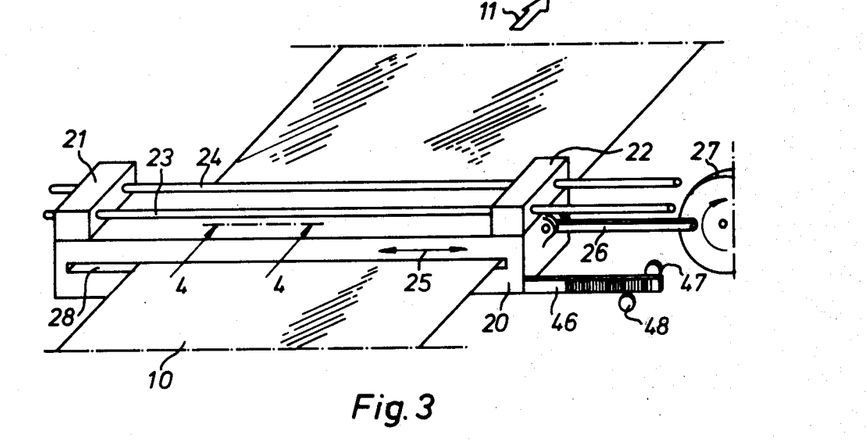
FIG. 3 is a diagrammatic isometric view of a first embodiment of a device in accordance with the invention for transversely scanning a moving web.

FIG. 3 is a diagrammatic isometric view of a device for transversely scanning a moving web. The device comprises a boxlike frame 20 that is slideably suspended by means of two guides 21 and 22 on two horizontally spaced, fixed parallel rods 23 and 24.

It will be understood that the illustrated suspension means may be replaced by any known other suspension or guide mechanism that enables the frame to carry out a scanning movement in the direction indicated by the arrow 25.

The transverse position of the frame with respect to the web 10 is controlled by a crank 26 that is pivotally fitted to one end of the frame and to a drive wheel 27 that may continuously rotate at a constant speed. The web 10 is passed through the device through a slotlike opening 28 along a path that is determined by the tangent plane to two rollers (not shown), one being located upstream and the other downstream of the device.

Within the frame there are mounted several detection units next to each other at equal intervals, each covering a section of the width of the web. One such unit is diagrammatically illustrated in the vertical cross-sectional view of FIG. 4, and the vertical longitudinal sectional view of FIG. 5.

Figure 4:
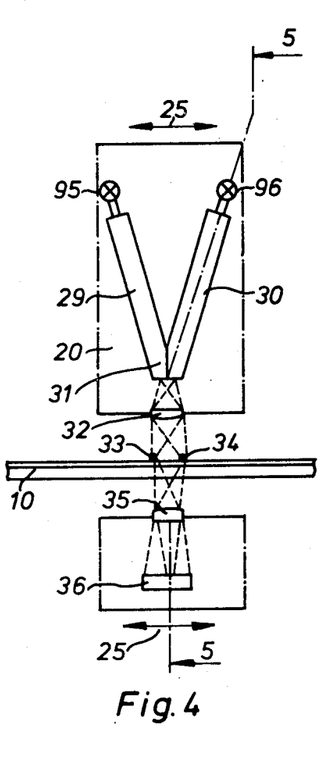
FIG. 4 is a partial vertical section on line 4—4 of FIG. 3.
Figure 5:
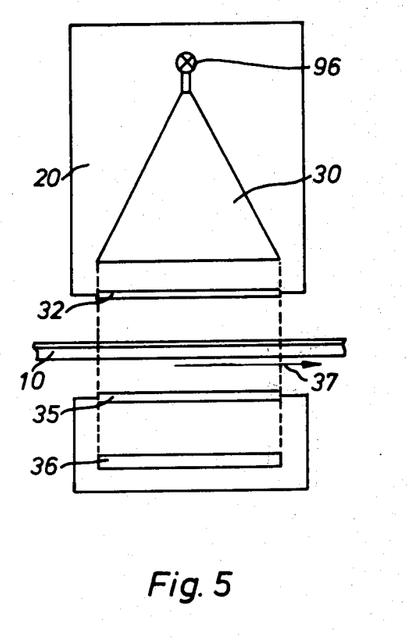
FIG. 5 is a section on line 5—5 of FIG. 4.

The unit comprises two so-called fishtail optics 29 and 30 which are fiber optic assemblies in which the fibers are bundled at one extremity to a bundle with a circular cross-section, and wherein the fibers diverge towards the other extremity to form a line on which the single fibers are ranged adjacent to each other. The two fishtail assemblies have been ground at their lower ends to form an interface 31 where they are adhered to each other. A rodlike lens 32 with a semi-circular cross-section projects the lines of radiation at the lower ends of the fishtails on the web in the form of the two lines of radiant energy that have been represented by the solid points 33 and 34, respectively. The radiant energy may be produced by any suitable source such as an incandescent bulb, a light-emitting diode (LED), or the like. In the present case, two LED's 95 and 96 were placed in face of the upper ends of the corresponding fishtail optics.

Radiation from both lines 33 and 34 that is transmitted through the web may be bundled by a second rodlike lens, such as lens 35 and is converged onto an elongate photocell 36. The sources of radiation as well as the photocell carry out an oscillating motion as indicated by the arrows 25. The amplitude of said oscillation is that of the oscillating amplitude of the frame 20 shown in FIG. 3.

It should be noted that several units such as the one illustrated in FIG. 4 are mounted at equal distances from each other within the frame 20, and that the distance between two successive units should be smaller than the amplitude of oscillation of the frame in order to completely scan the web in transverse direction. As the web moves away from the reader in the illustration of FIG. 4, the web movement is towards the right in FIG. 5 as shown by the arrow 37.

Figure 6:
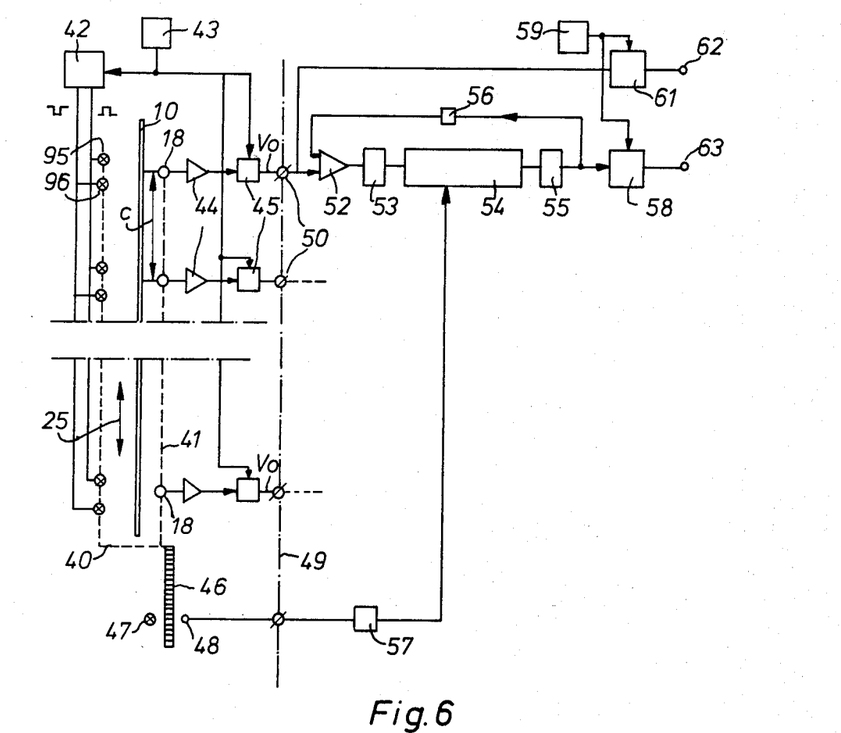
FIG. 6 is the electronic block circuit of the device according to FIGS. 3 to 5.

The electronic block circuit of the device is shown in FIG. 6. A web 10 that moves in a direction normal to the plane of the drawing is scanned by pairs of light sources 95 and 96 that produce adjacent pairs of lines of radiant energy on the web as shown in detail in FIG. 4. Corresponding photocells 18 receive the radiation transmitted through the web and are bodily coupled as illustrated by the broken lines 40 and 41 with the light sources in order to carry out an oscillating displacement with respect to the web in the direction of the arrow 25.

The light sources of each pair of sources are alternatively energized by a source 42 in response to an electronic oscillator 43. The output signals of the photocells are amplified by amplifiers 44 and synchronously demodulated by corresponding demodulators 45 and are likewise controlled by the oscillator 43. The amplifiers 44 may comprise a high-pass filter with a breakpoint at 20 Hz for 6 db attenuation.

The frame of the device is further provided with a pulse-generator 46 in the form of a glass strip that is provided with a great number of spaced fields capable of periodically absorbing the radiation from a stationary light source 47 that is directed to a photocell 48. The vertical dash and dot line 49 represents a wall of the oscillating frame at which all the electrical terminals may be grouped and connected by means of a flexible band comprising different separate conductors with the remaining electronic circuit of the device which is mounted in practice in a stationary column beside the oscillating frame.

It will be clear that upon oscillation of the frame with the light sources and the photocells, no electric output signals $V_o$ occur at the terminals 50 if a defect-free web is being examined. As a matter of fact, the blocklike energizing of the pairs of light sources 95 and 96 produces output signals of the photocells which have equal magnitude, polarity and width so that synchronous demodulation of them by the circuits 45 produces a zero output voltage. In case however, a pair of light sources scans a streaklike defect, the amplitude of the successive output signals of the corresponding photocell will no longer be equal for the two light sources during their passage over a line defect of the web so that the resulting demodulated signal will no longer be zero. The same applies equally for the other pairs of light sources and the corresponding photocells that each cover a section of the width of the web, as indicated by the distance c.

Figure 7:
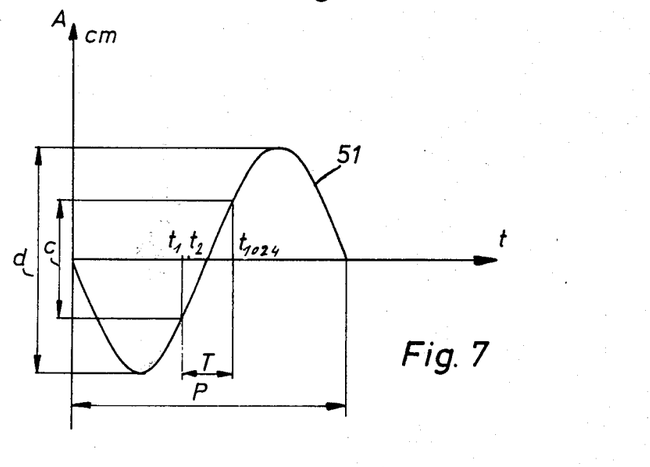
FIG. 7 illustrates the sinusoidal displacement of the device according to FIG. 3, and the operative detection zone within said sinusoidal displacement.

In connection with this distance c, it should be noted that this is a fraction only of the peak-to-peak amplitude of the oscillation of the frame 20. This is illustrated in the diagram of FIG. 7 where the distance d represents the peak-to-peak amplitude of the frame 20 and the distance c represents the effective scanning width of each photocell. As a consequence of the mentioned difference between d and c, the distance c covers a portion of the curve 51 that represents the sinusoidal motion of the frame, that deviates not quite much from a line, whereby the corresponding speed of the frame during measuring is nearly uniform.

As a consequence of the frame amplitude d that is greater than the distance c between two adjacent measuring units, overlapping measurement occurs. The electronic circuit is, however, so arranged (not shown) that the output signals of overlapping measurements of adjacent web sections are not processed.

The right hand portion of the drawing of FIG. 6 shows an electronic correlation circuit for improving the signal-to-noise ratio of the output signal of a photocell 18. It should be noted that actually there is one such correlation circuit for each photocell circuit.

The electronic correlation circuit comprises an addertype amplifier 52, an analog-to-digital converter 53, a delay line 54 in the form of an 8 bit shift register with 1024 positions, a digital-to-analog converter 55, and a feedback element 56. The adder sums the incoming signals with a delayed output signal which has been multiplied by a feedback gain K which is strictly less than unity. The delay line 54 is controlled in synchronism with the scanning of the web by pulses produced by the pulse generating strip 46 that comprises in this specific embodiment 1024 pairs of light absorbing and light transmission areas. The signals of the photocells 48 are appropriately shaped by a pulse shaper 57.

The operation of the circuit is as follows. An input signal that occurs at a time $t_1$, see FIG. 7, is stored in the first stage of the shift register 54 until at a time $t_2$ the pulse generator 46 controls the shift register to shift its information over one place whereby the first signal is transferred to the second stage, and the new signal that occurs at the time $t_2$ is entered into the shift register in the first stage. The same procedure continues until the generator 46 has been displaced over a distance c i.e. at the time $t_{1024}$ what means that the scanning of the respective section of the web has been completed, and that the signal that was produced at a time $t_1$ has now been shifted to the 1024th position of the shift register.

The circuit is so arranged (not illustrated) that during the returning movement of the frame the shift register remains inoperative. At the second scanning of the web, a pulse from the generator 46 at a time $t_1$ transfers the output signal (at the 1024th stage) of the shift register to the first stage where it is added to the new signal that occurs at the same transverse position of the web as the position where said added signal is produced, etc. The same operation is continuously repeated at least 5 times thereby to increase the signal-to-noise ratio by a factor up to 12 db.

The output signals of each correlator circuit are fed to a trigger 58 where they are compared with a reference signal from a reference signal generator 59. In case the difference between the two signals exceeds a predetermined value, the output signal at terminal 63 may, as mentioned already in the introduction of the specification, either directly control a warning mechanism, or it may be stored either in analog or in converted digital form in a memory together with the exact address of the location of the defect on the web. One part of said address is formed by the pulse number of the generator 46 which indicates the transverse location of the defect on the web. Another part of the address may be formed by the number from a counter that counts the number of meters of the web which have been unwound from a roll. Such counter is usually reset at zero at the starting of the treatment, for example coating, of each new roll of web. Still another part of the address may be an identification number for the device that detected the object. The circuit comprises further a second trigger 61 that is directly connected with the input terminal 50 and that serves for the instant signalling at a terminal 62 of defects that are so severe that they need not a repeated circulation through the correlation circuit, with the corresponding delay, to reach a level at which sufficient signal-to-noise distinction has been obtained.

It should finally be noted that the active operation of the device, namely from a time $t_1$ to a time $t_{1024}$, is a fraction only of the period of one complete scanning.

In consequence the examination of the moving web occurs interruptedly considered in the longitudinal direction. Taking into account, however, that the device according to the invention is intended for the identification of streaklike defects of protracted extent, this lack of continuity of the measurement in the longitudinal direction of the web is without any importance.

The following data illustrate the operation of the described device that was used for the inspection of a wet coating of silver halide that was applied by means of a slide hopper to a polyethylene terephthalate film having a width of 1.70 m.

| | |
|---|---|
| Scanning amplitude d of the frame 10 | 35 cm |
| Effective scanning width c | 21.5 cm |
| Oscillation period P | 2.4 s |
| Effective scanning time T | 0.6 s |
| Number of optical units | 8 |
| Width of a line of radiant energy on the web | 1 mm |
| Length of a line of radiant energy | 10 cm |
| Distance between the two lines of a pair of lines | 1 mm |
| Frequency (f) of the oscillator 43 (that is also the inspection frequency) | 10 kHz |
| Number of signal comparisons during one scan (T×f) | 6000 |
| Number of signal circulations through the correlator | 5 |
| Corresponding observation time | 12 s |
| Number of signal observations by the correlator for one scan | 1024 |
| Detectable streaklike thickness variations | 0.1% |
| Variation in the output signals for a film fluttering of 1 mm at a frequency above 20 Hz | 0.5% |

Components used:
Lamps 35 and 36: LED type GE manufactured by FIRE DIVISION International Audio Visual Inc.
Photocells 18: PIN-L4 manufactured by United Detector Technology
Spectral band of measurement: 880 nm wavelength.

It should be noted that the multiplicity of signal comparisons that is carried out by the measuring device with the alternately operated pairs of lamps 95 and 96, is much greater than the number, namely 1024, of discrete signals into which the output voltage $V_o$ of the measuring device is divided for carrying out the correlation. It can thus be said that finally the separating power of the device is 1024 points for each web section being examined. Whereas this number is largely sufficient for many applications, it should be understood it can easily be increased by using instead of pulse strip 46 another pulse strip capable of producing a larger number of pulses. It is evident that the number of the positions of the shift register 54 should correspondingly be increased. Another point that has to do with the sensitivity of the device is that the ADC convertors 53 and the DAC convertors 55 are 8 bit devices whereby 256 (that is $2^8$) distinct levels of the signals $V_o$ can be transmitted. It is clear that by using converters with a number of bits $2^n$, wherein n is greater than 8, the sensitivity for small signal variations can further be increased.

Figure 8:
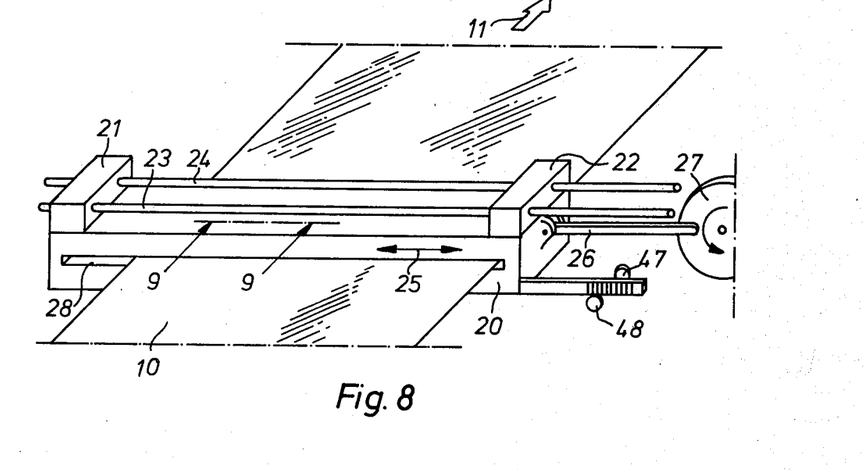
FIG. 8 is a diagrammatic isometric view of a second embodiment of a device according to the invention for transversely scanning a moving web.
Figure 9:
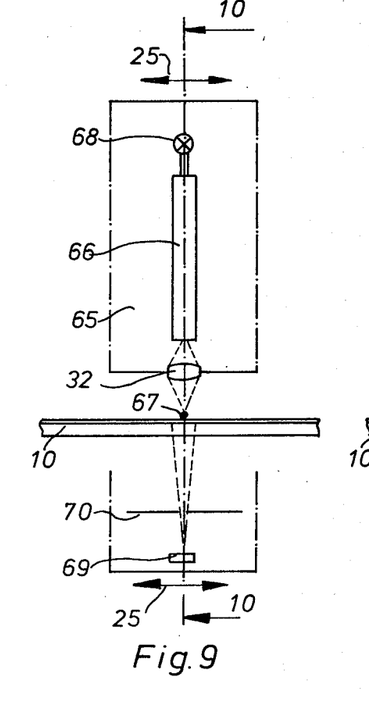
FIG. 9 is a partial vertical section on line 9—9 of FIG. 8.
Figure 10:
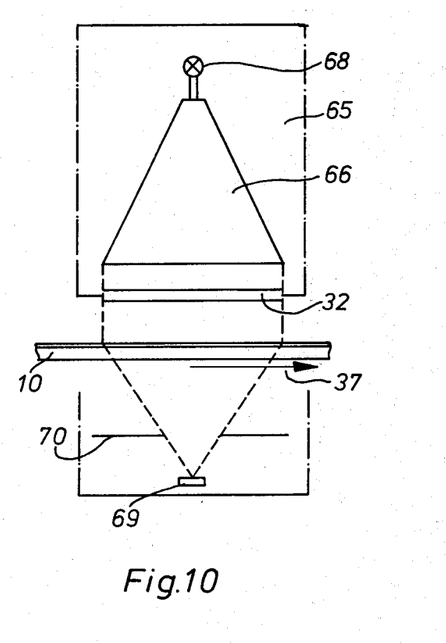
FIG. 10 is a section on line 10—10 of FIG. 9.

A second embodiment of the device according to the invention is illustrated in FIGS. 8, 9 and 10. The substantial difference between the second and the first embodiment of the device resides in that in the second embodiment a plurality of single lines of radiant energy are used to transversely scan a web instead of a plurality of pairs of lines, and that electronic means is provided to simulate, so to say, a second line for each said single line.

Referring to FIGS. 8 to 10 wherein parts that are identical to these of FIGS. 3 to 5 have been indicated by the same reference numerals, an oscillating frame 20 is provided with several units 65 that are fixedly mounted within the frame at equal distances and that each comprise one fishtail optic 66 for producing a line of radiant energy that is projected by a rodlike lens 32 on the web 10 as a line 67. A light source 68 provides the radiant energy at the input of the fishtail optic. At the opposite side of the web path there is provided a photocell 69 with a rather wide angle of field that is limited in the plane of FIG. 9 by a shield 70 to a rather narrow angle, merely sufficient to merely "see" the transmitted line 67 of radiant energy.

Referring to the longitudinal sectional view of the unit in FIG. 10, it may be seen that the shield 70 has an elongated opening thereby to permit the photocell 69 to "see" the complete length of the line of radiant energy produced on the web 10.

Figure 11:
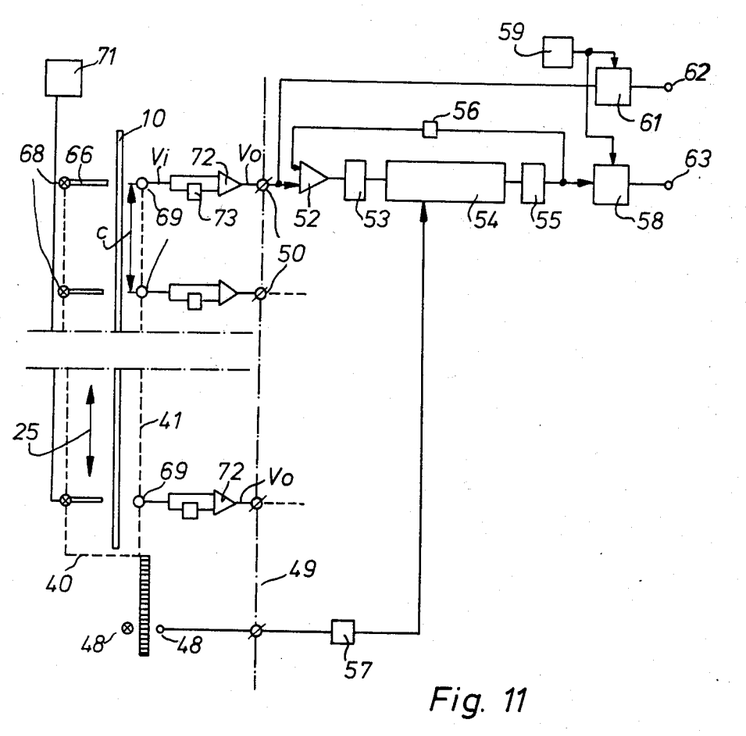
FIG. 11 is the electronic block circuit of the device according to FIGS. 8 to 10.

A diagrammatic electronic block circuit that illustrates the principle of the measuring device is illustrated in FIG. 11. A web 10 that moves in a direction normal to the plane of the drawing is scanned by light sources 68 that produce lines of radiant energy on the web as shown in detail in FIGS. 9 and 10, and that are spaced over regular intervals c. Corresponding photocells 69 receive the radiation transmitted through the web, and are bodily coupled as illustrated by the broken lines 40 and 41 with the light sources in order to carry out an oscillating displacement with respect to the web in the direction of the arrow 25. The light sources 68 are continuously energized by a source 71.

Each photocell 69 is coupled directly to one input terminal of a differential type amplifier 72, and indirectly over a delay line 73 to the second input terminal of the amplifier 72.

If $\tau$ is the time delay of the delay line 73, then the output voltage $V_o$ of the circuit may be written as follows if the input voltage is $V_i(t)$ at a given moment t:

$$V_o = V_i(t) - V_i(t-\tau) \tag{1}$$

The output signal $V_o$ is thus the difference between two measured values that are separated in the transverse direction of the web over a distance b in accordance with the equation:

$$b = S/P \cdot \tau \cdot 10^{-2} \tag{2}$$

wherein:
b is the distance in $\mu$m on the web between two measurements,
S is the width of scanning in cm (equal to c),
P is the scanning period (the time between two successive measurements) in sec.,
$\tau$ is the time delay in $\mu$ sec.

The output voltages $V_o$ obtained in the described way are the full equivalent of the voltages obtained by means of the pairs of lines of radiant energy in the device of FIG. 3, and thus the signals that appear at terminals 50 of the frame, may undergo a correlation treatment by a circuit as described hereinbefore in detail with reference to FIG. 6.

The following example illustrates the operation of the described delay circuit.

For S=6 cm, P=0.2 s, and τ=100 μs, then b=30 μm.

Figure 12:
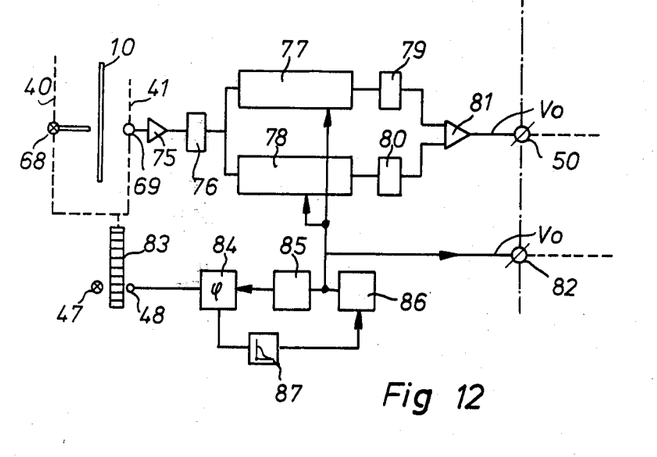
FIG. 12 is the electronic block circuit of the means for delaying the output signal of each photocell of the device according to FIG. 11.

Referring to FIG. 12, an electronic block circuit is shown wherein the principle of delaying a signal as described for FIG. 11, is realized by means of usual components.

The output signal of a photocell 69 is amplified in a pre-amplifier 75 and then converted in digital form by the analog-to-digital converter 76. Blocks 77 and 78 are two equal 8-bit shift registers that in the present example have 1024 positions. The outputs of both shift registers are put in analog form by the digital-to-analog converters 79 and 80, and the output signals thereof are fed to the input terminals of a differential type amplifier 81. The output signal of the amplifier 81 may further be correlated as described hereinbefore with reference to FIGS. 6 and 11 to improve the signal-to-noise ratio. The correlator circuit may receive its synchronization pulses from a connection 82 at which the pulses that represent the successive 1024 positions of the frame are present. The latter pulses are not directly obtained as in the case of the device according to FIG. 3 but on the contrary they are obtained by electronic multiplication as will be explained now.

The pulse generating strip of the present device has a much smaller length than the corresponding strip of the device of FIG. 3, since the device of FIG. 12 was designed for a much smaller oscillation amplitude. Therefore, it was easier to provide only 128 successive light-absorbing and light-transmitting areas on the strip, and to treat the output signal of the photocell 48 in an electronic way to multiply said signal frequency by a factor 8 to obtain 1024 pulses per scan. This is done by means of a phase comparator 84, an electronic divider 85 dividing the frequency of a voltage-controlled oscillator 86 by a factor 8 and a low pass filter 87. In the mentioned way, the oscillator 86 is perfectly synchronized by the strip 83 to produce a frequency that is by a factor 8 greater than the frequency produced by the strip 83.

The operation of the two delay lines is as follows.

The shift register 77 is controlled by 1024 successive pulses to shift the information from its input to its output.

The shift register 78 is controlled by 1024-N pulses so that at the output of the amplifier 81 the signal difference is obtained for two measurement positions that are separated in the transverse direction of the web over a distance of:

$b = S \cdot N / 1024.$

If the electronic circuit is so arranged that N may be adjusted at will between 0 and 1024, it will be understood that the system may be readily adjusted to obtain optimum defect identification sensitivity in accordance with the curve of FIG. 2 with b/a=0.5.

The following data illustrate the operation of the described device that was used in combination with the correlation circuit of FIG. 11 for the control of a sorting mechanism for radiographic film sheets that were cut from a polyethylene terephthalate web which was provided with a light-sensitive silver halide coating on both its sides.

| | |
|---|---|
| Scanning amplitude d of the frame | 12 cm |
| Effective scanning width c | 6 cm |
| Oscillation period P | 0.2 s |
| Effective scanning time T | 0.033 s |
| Number of optical units | 8 |
| Width of a line of radiant energy on a sheet | 0.2 mm |
| Length of a line of radiant energy | 5 cm |
| Time delay τ between two successively compared signals | 32 μs × N |
| Number of signal comparisons during one scan | 1024 - 2N |
| Number of signal observations by the correlator | 5 |
| Corresponding observation time | 1 s |
| Detectable streaklike thickness variations | 0.1% |
| Variation in the output signals for a sheet fluttering of 1 mm at a frequency above 20 Hz | 0.5% |

Components used:

Lamps 68: 999079/44 manufactured by WELCH-ALLYN

Photocells: SD 3422 manufactured by SPECTRONICS

Spectral band of measurement: 900 mm

It will be understood that the present invention is not limited to the described embodiments.

The method and the device according to the invention may also be used for measuring in reflection rather than in transmission.

The oscillation of the frame means may occur by other mechanisms than by the simple crank and connecting rod mechanism, for instance by a threaded spindle, a cable mechanism, etc.

Other types of delay lines may be used in the electronic circuit, for instance magnetic delay lines, acoustic delay lines, charge coupled devices (CCD's), etc.

In case optical units producing pairs of radiant energy are used, means may be provided to adjust the distance between the lines of each pair of lines thereby to obtain maximum sensitivity for b/a as explained hereinbefore with reference to FIG. 2.

The pulse generator that operates in synchronism with the frame oscillation may be of another type than an optical one, for instance a magnetic type.

The light sources 35, 36 and 68 may be any type of source capable of producing radiation which may be modulated by a streaklike defect in a sheet material or in a coated layer on such sheet material.

We claim:

1. Method of inspecting sheet material for streak-like defects during travel of such material along a certain path, which method comprises the following steps: scanning across at least part of the width of said path with one or more beams of radiation, each beam of which at any given instant irradiates a narrow zone which is elongated in the direction of travel of the material; receiving radiation which has been transmitted through or reflected by the successively irradiated zones of the material on a photocell; deriving from such photocell a multiplicity of sequential signals, each representative of a particular one of said elongated narrow zones; and, comparing said successive signals with a preceding or following signal to establish amplitude differences between the thus-compared signals and from said differences to indicate the presence of said defects.

2. Method according to claim 1, wherein said derivation and comparison of signals is carried out by projecting two narrow elongated beams of radiant energy on the moving sheet material at closely spaced parallel positions, alternately and repeatedly energizing one beam and extinguishing the other beam during the scanning of the moving sheet material with said pair of beams, receiving the reflected or transmitted energy of either beam on said one photocell, and demodulating the output signal of the photocell in synchronism with the switching frequency of both beams of radiant energy, thereby to obtain an output signal.

3. Method according to claim 1, wherein said derivation and comparison of signals is carried out by delaying an output signal of the photocell by a constant time delay $\tau$, comparing the delayed output signal of the photocell with the instant output signal that is produced after such time delay $\tau$, thereby to obtain an output signal responsive to the scanning of said sheet material when defects are present.

4. Method according to claim 3, wherein said time delay $\tau$ corresponds with a lateral spacing b between two zones of the web under inspection according to the formula $b = S/T \cdot \tau$ wherein S is the width scanned and T is the scanning duration.

5. Method according to claim 4, wherein said distance b is comprised between 0.15 and 1 times the width a of a streaklike defect.

6. Method according to claim 4, comprising adjusting said distance b in operation of the method to obtain maximum sensitivity for a given type of streaklike defect.

7. Method according to claim 1 comprising improving the signal-to-noise ratio of said output signals by electronic correlation.

8. Device for identifying streaklike defects in a moving sheet material, comprising:
    frame means mounted for oscillation in a direction transverse to the direction of movement of the sheet material,
    at least one source of radiant energy mounted on said frame and arranged for producing on the surface of a moving sheet material, at least one elongated beam of radiant energy extending in a direction parallel with the direction of movement of the sheet material,
    at least one photocell mounted on said frame and arranged for receiving radiation from a corresponding beam of radiant energy after such beam has been transmitted by or reflected from the moving sheet material,
    means for oscillating said frame means with an oscillation amplitude that is at least equal to the width of the portion of the sheet material being measured, and
    comparatory means for comparing during each oscillation the signals in each of a multiplicity of pairs of distinct output signals from each photocell with each other, the signals in each pair being thus compared being separated by a given time interval, to detect a difference in amplitude between each such two signals and thereby the presence of a streaklike defect.

9. Device according to claim 8, wherein said means for oscillating said frame means is arranged for sinusoidally oscillating said frame means with a peak-to-peak amplitude of at least three times the distance between two adjacent beams, or two adjacent pairs of beams, of radiant energy.

10. Device according to claim 8, wherein the ratio of the length to the width of a beam of radiant energy produced on the moving sheet is between 20 and 100, and wherein the width of a beam of radiant energy produced on the web ranges between 0.05 and 3 mm.

11. Device according to claim 8, including means for controlling said time interval which comprises a second energy source for producing close to each elongated beam of radiant energy a second, parallel beam of radiant energy, thereby to provide on the surface of said moving sheet material at least one pair of beams of radiant energy, each such photocell being arranged to be responsive to energy from a corresponding pair of such beams, and wherein said sources of radiant energy of each beam pair are alternatingly activated and extinguished, thereby to alternatingly produce first one and then the other line of said beams on the surface of the moving sheet material.

12. Device according to claim 11, which comprises an oscillator controlling the switching from one beam of each pair to the other, and a synchronous demodulator for each such photocell for demodulating the output signal thereof, said demodulator being synchronously controlled by said oscillator.

13. Device according to claim 8, including means for controlling said time interval, which means comprises a delay line in the output of each photocell, for providing a delayed signal therefrom, and a differential type amplifier to which said delay line is connected for comparing each delayed signal of a photocell with the instant output signal of the photocell occurring at the moment of comparison.

14. Device according to claim 13, wherein the time delay of said delay line is adjustable.

15. Device according to claim 13, wherein said delay line comprises two shift registers the inputs of which are connected in parallel, one shift register comprising a number of steps corresponding with the number of discrete measurements to be carried out during each scan, and the other shift register comprising a smaller number of steps, the outputs of both registers being connected to the respective inputs of a differential type amplifier.

* * * * *